United States Patent
Fujii et al.

(10) Patent No.: US 8,106,371 B2
(45) Date of Patent: Jan. 31, 2012

(54) CHARGED PARTICLE IRRADIATION SYSTEM AND IRRADIATION PLANNING EQUIPMENT

(75) Inventors: Yusuke Fujii, Hitachi (JP); Kazuo Hiramoto, Hitachiohta (JP); Yoshihiko Nagamine, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 145 days.

(21) Appl. No.: 12/715,098

(22) Filed: Mar. 1, 2010

(65) Prior Publication Data
US 2010/0243911 A1 Sep. 30, 2010

(30) Foreign Application Priority Data

Mar. 31, 2009 (JP) ................ 2009-084004
Feb. 22, 2010 (JP) ................ 2010-035546

(51) Int. Cl.
*A61N 5/10* (2006.01)

(52) U.S. Cl. ................................ 250/492.3

(58) Field of Classification Search ............... 250/492.3, 250/398
See application file for complete search history.

(56) References Cited

U.S. PATENT DOCUMENTS

| 6,617,598 B1 * | 9/2003 | Matsuda ............ 250/492.3 |
| 2006/0231775 A1 | 10/2006 | Harada |
| 2008/0191142 A1 | 8/2008 | Pedroni |

FOREIGN PATENT DOCUMENTS

| EP | 1 477 206 A1 | 11/2004 |
| JP | 2006-288875 A | 10/2006 |
| JP | 2008-145627 A | 7/2008 |
| WO | 2007/079854 A2 | 9/2007 |

* cited by examiner

*Primary Examiner* — Kiet Nguyen
(74) *Attorney, Agent, or Firm* — Mattingly & Malur, PC

(57) ABSTRACT

In a charged particle irradiation system, forming a uniform dose distribution is required by irradiating a moving irradiation object through beam scanning and energy stacking. The charged particle irradiation system includes an ion beam generator 1 from which an ion beam is extracted with a target beam current value thereof set; an irradiation nozzle 21 having scanning magnets 23, 24 and an energy filter 26, the irradiation nozzle 21 for irradiating an irradiation object with the ion beam; and an irradiation object monitoring unit 66 for measuring a position of the irradiation object and outputting signals that vary with time according to displacement of the irradiation object. The charged particle irradiation system determines extraction timing of the ion beam based on the signal outputted from the irradiation object monitoring unit 66 and sequentially changes energies of the ion beam to thereby perform a repainting irradiation with each of the energies.

10 Claims, 10 Drawing Sheets

CHARGED PARTICLE IRRADIATION SYSTEM AND IRRADIATION PLANNING EQUIPMENT

BACKGROUND OF THE INVENTION

1. Field of the Invention

The present invention relates to particle beam irradiation systems and, more particularly, to a charged particle irradiation system that treats a tumor or other affected part by irradiating the affected part with a charged particle beam.

2. Description of the Related Art

In a known therapy method, a cancer or other affected part of a patient is irradiated with a charged particle beam (ion beam) of, for example, either a proton or carbon ion beam. A charged particle irradiation system used in such a therapy typically includes an ion beam generator, a beam transport line, and an irradiation room. An ion beam generated by the ion beam generator is transported to the irradiation room by the beam transport line and reaches an irradiation nozzle in the irradiation room. The ion beam that reaches the irradiation nozzle is thin. The irradiation nozzle includes a scanning magnet that scans the ion beam traveling therethrough. In order to form a uniform dose distribution over an irradiation target, such as a cancer tumor, the scanning magnet of the irradiation nozzle can irradiate an entire irradiation target with the ion beam that is scanned in a direction (lateral direction) perpendicular to a beam axis. Irradiating the irradiation target with this ion beam forms a dose distribution that has a peak at a specific depth as determined by energy of the ion beam. The peak of the dose distribution is called a bragg peak. Because the bragg peak has a narrow spread of a few mm in a depth direction, ion beam irradiations with varying energies achieve uniform irradiation of the target.

A method of widening the dose distribution called a scanning irradiation method to which the present invention pertains uses a scanning magnet to scan the ion beam to thereby widen the dose distribution in the lateral direction and change the energy to thereby widen the dose distribution in the depth direction. The scanning irradiation method offers a benefit of an efficient use of the ion beam thanks to a small energy loss of the ion beam in the irradiation nozzle. Due to the beam scanning and energy change involved in the method, however, the affected part or other irradiation target is irradiated so as to be sequentially painted. If the irradiation object is displaced during irradiation, for example, if the affected part is displaced as the patient breathes, a uniform dose distribution may not be formed.

JP-2008-154627-A discloses a method for performing repainting irradiation. In this method, a displacement waveform representing a displacement amount of the irradiation object is obtained in advance and, only when the irradiation object is in a predetermined phase during irradiation, a dose is divided and delivered in a plurality of times. If the displacement waveform changes radically from what was obtained in advance, the method stops irradiation and resumes irradiation at the same phase in the next cycle to thereby form a desired dose distribution.

JP-2006-288875-A discloses a charged particle irradiation system that is controlled such that the scanning magnet disposed in the irradiation nozzle bends the ion beam in a direction perpendicular to a direction in which the ion beam travels and irradiation is repeated in units of a spiral cycle. The charged particle irradiation system is controlled such that, upon repainting irradiation, the scanning magnet controls an irradiation position of the ion beam in units of a spiral cycle so as not to allow irradiation of the ion beam to be interrupted in the middle of the spiral cycle, thereby achieving a uniform dose distribution.

In the charged particle irradiation system based on the scanning irradiation method according to the present invention, means is provided for forming a uniform dose distribution in a moving irradiation target.

According to the method disclosed in JP-2008-154627-A, irradiation time may be longer by irradiation interruption, if the displacement waveform of the irradiation object is not stable.

SUMMARY OF THE INVENTION

The present invention provides a charged particle irradiation system which includes an energy filter and performs repainting irradiation and gate irradiation to form any desired irradiation field relative to a moving irradiation object. Uniformity in the depth direction is achieved by making a bragg peak shape mild using the energy filter and through the repainting irradiation. To achieve uniformity in the lateral direction, one-plane irradiation is completed without being interrupted in the middle of the irradiation, in consideration of the fact that effect is only little from irradiation outside the gate for a short period of time even after the gate is terminated.

According to the present invention, a desired dose distribution can be formed even if the irradiation object is displaced. Enlarging the width of the bragg peak by using the energy filter, in particular, helps minimize a change in the dose relative to movement of the bragg peak. In addition, the number of energies used can be reduced. This elongates time to irradiate with a single energy within the same irradiation time as in the past, allowing a number of times of repainting irradiations to be performed.

BRIEF DESCRIPTION OF THE DRAWINGS

The present invention will be described hereinafter with reference to the accompanying drawings.

DESCRIPTION OF THE PREFERRED EMBODIMENTS

An embodiment of the present invention will be described below with reference to the accompanying drawings.

First Embodiment

Figure 1:
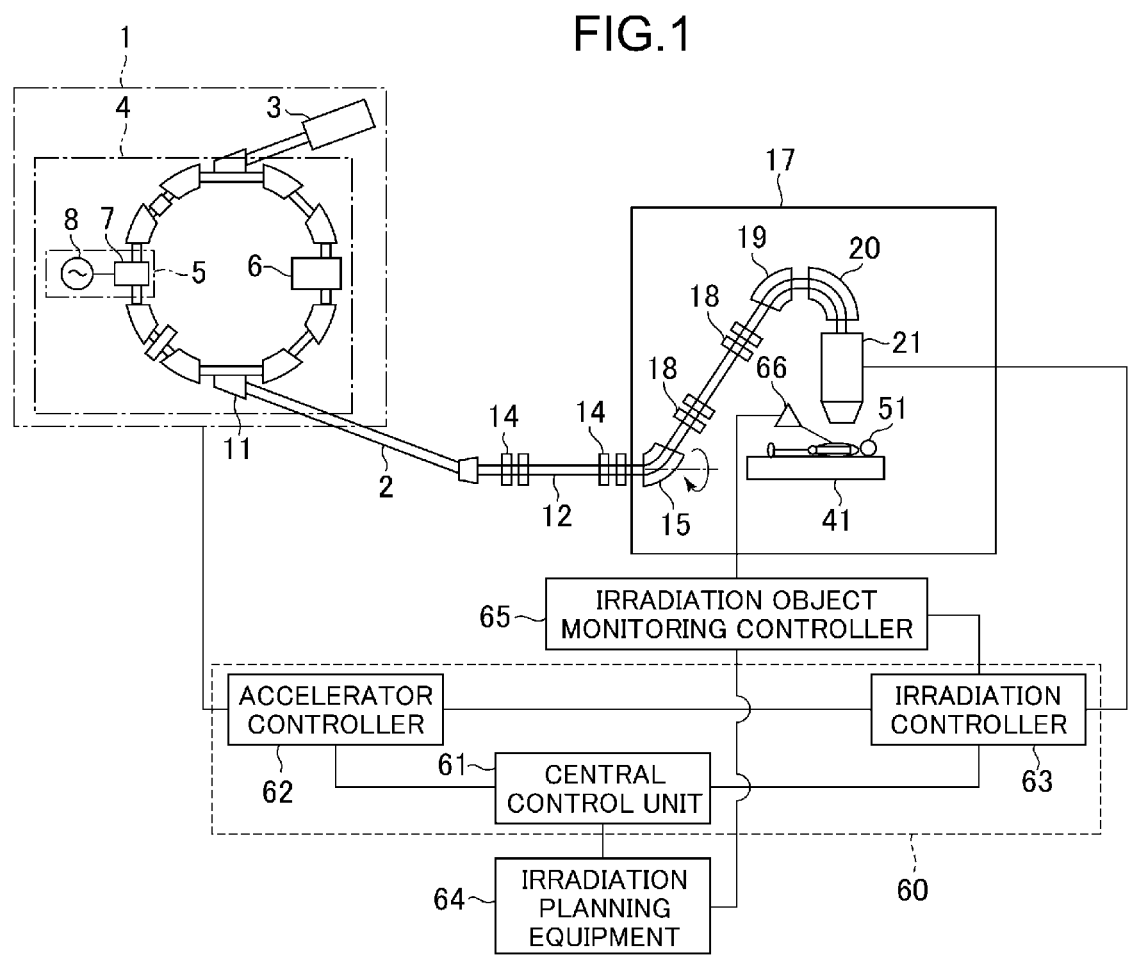
FIG. 1 is a diagram showing a general arrangement of a charged particle irradiation system according to a first preferred embodiment of the present invention.

A charged particle irradiation system according to a preferred embodiment of the present invention will be described with reference to FIG. 1. The preferred embodiment of the present invention assumes that an irradiation object 51 is specifically a patient and an irradiation target 52 is an affected part in the patient. The irradiation object of the irradiation method according to the embodiment of the present invention does not necessarily have to be a human.

The charged particle irradiation system according to the preferred embodiment of the present invention includes an ion beam generator 1, a beam transport line 2, an irradiation nozzle 21, an irradiation room 17, and a control system 60. The beam transport line 2 connects between the ion beam generator 1 and the irradiation nozzle 21. The charged particle irradiation system is connected to irradiation planning equipment 64.

The ion beam generator 1 includes an ion source (not shown), a linear accelerator 3 (preaccelerator), and a synchrotron 4. The synchrotron 4 includes a radiofrequency acceleration unit 5 and an acceleration unit 6. The radiofrequency acceleration unit 5 includes an extraction radiofrequency electrode 7 and an extraction radiofrequency power supply 8. The extraction radiofrequency electrode 7 is disposed on a closed orbit of the synchrotron 4. The extraction radiofrequency power supply 8 is connected to the extraction radiofrequency electrode 7. The acceleration unit 6 includes a radiofrequency acceleration cavity (not shown) and a radiofrequency power supply. The radiofrequency acceleration cavity is disposed on a closed orbit of an ion beam. The radiofrequency power supply applies radiofrequency power to the radiofrequency acceleration cavity. An extraction deflector 11 connects between the synchrotron 4 and the beam transport line 2.

The beam transport line 2 includes a beam path 12, a quadrupole magnet 14, a quadrupole magnet 18, a bending magnet 15, a bending magnet 19, and a bending magnet 20. The beam path 12 is connected to the irradiation nozzle 21 disposed in the irradiation room 17.

The irradiation room 17 includes a rotating gantry (not shown) that can change the direction in which the irradiation object 51 is irradiated with the ion beam. The irradiation nozzle 21 rotates with the rotating gantry. Further, the irradiation room 17 includes the irradiation nozzle 21, a couch 41 (support) for supporting the irradiation object, an irradiation object monitoring unit 66 that measures displacement of the irradiation object 51. Additionally, the irradiation object 51 is placed on a bed called the couch 41 that is freely movable three-dimensionally.

Figure 2:
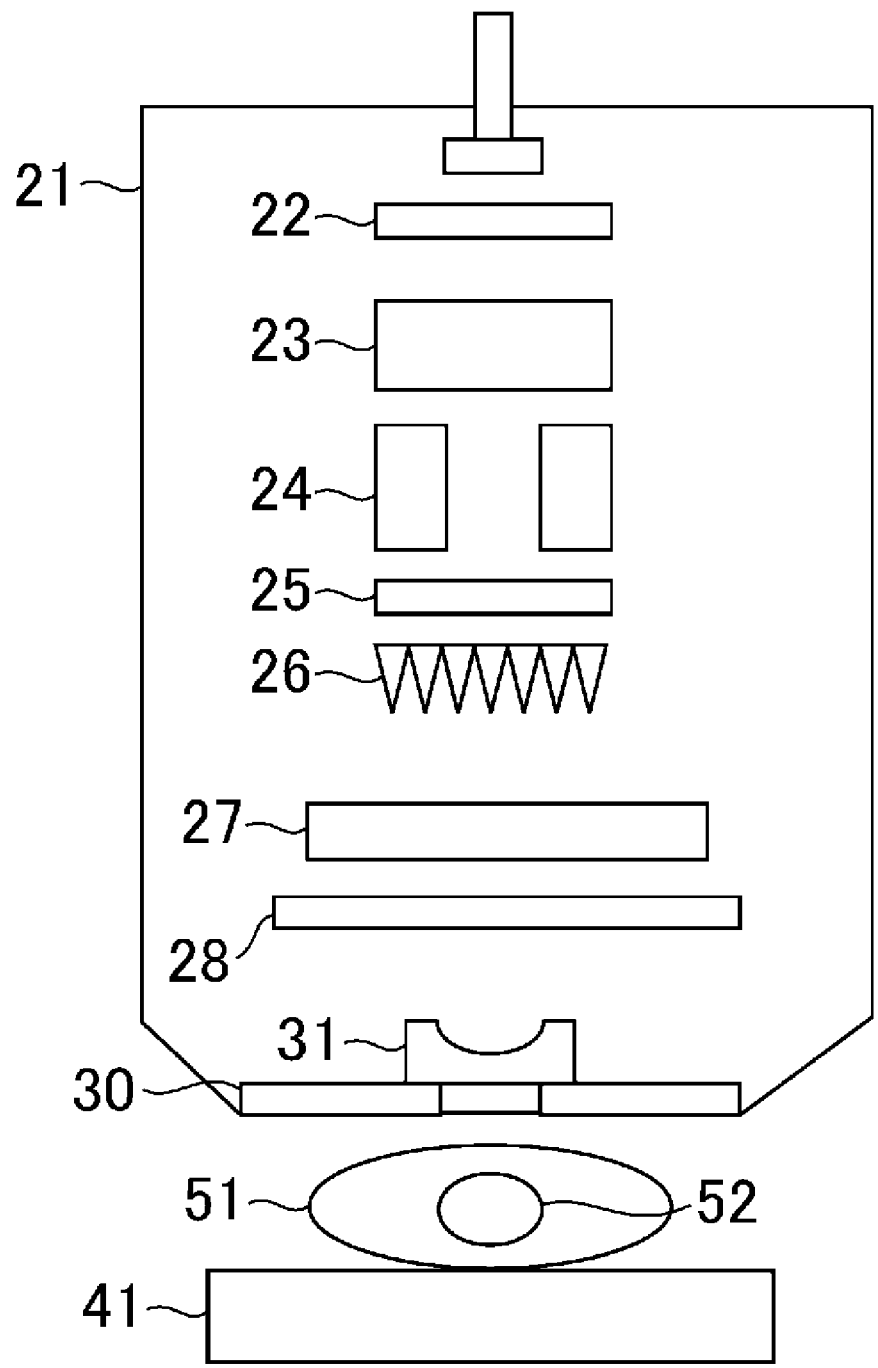
FIG. 2 is a transverse cross-sectional view showing an arrangement of an irradiation nozzle included in the charged particle irradiation system shown in FIG. 1.

The irradiation nozzle 21 will be described with reference to FIG. 2. The irradiation nozzle 21 includes a monitor 22, a Y-axis scanning magnet 23, an X-axis scanning magnet 24, a scatterer 25, an energy filter 26, an energy absorber 27, a monitor 28, a collimator 30, and a bolus 31, as seen from the upstream side in the beam travelling direction. The Y-axis scanning magnet 23 and the X-axis scanning magnet 24 scan the ion beam travelling therethrough in the lateral direction (in the X- and Y-axis directions). The lateral direction as the term is here used refers to a direction perpendicular to a beam axis. The energy filter 26 is wedge-shaped, which makes the ion beam dose distribution called the bragg peak mild in the depth direction. The scatterer 25 increases the ion beam passing therethrough in diameter. The monitors 22 and 28 measure flatness of the ion beam dose distribution, irradiation dose, beam position, and beam intensity (beam current value). The energy absorber 27 is used for fine-adjustments of beam energy. The collimator 30 matches the shape of the dose distribution of the ion beam in the lateral direction with that of the irradiation target 52. The bolus 31 adjusts an ion beam range for each lateral position to match the shape of the irradiation target 52.

Referring back to FIG. 1, the control system 60 includes a central control unit 61, an accelerator controller 62, and an irradiation controller 63. The central control unit 61 is connected to the accelerator controller 62 and the irradiation controller 63. In addition, the irradiation planning equipment 64 is connected to the central control unit 61 and an irradiation object monitoring controller (monitoring controller) 65. The accelerator controller 62 is connected to the ion beam generator 1 and controls devices included in the ion beam generator 1. The irradiation controller 63 is connected to the irradiation nozzle 21 and controls devices included in the irradiation nozzle 21. The irradiation controller 63 is connected to the irradiation object monitoring controller 65. The accelerator controller 62 is connected to the irradiation controller 63.

The central control unit 61 receives parameters required for irradiation from the irradiation planning equipment 64 and, based on these parameters, controls the accelerator controller 62 and the irradiation controller 63 to thereby control irradiation of the ion beam. The accelerator controller 62 uses a signal from the irradiation controller 63 to control the ion beam generator 1 and the beam transport line 2. The irradiation controller 63 receives signals from the irradiation nozzle 21 and the irradiation object monitoring unit 65 and controls the irradiation nozzle 21 and transmits signals, such as an extraction start signal, to the accelerator controller 62.

The charged particle irradiation system according to the preferred embodiment of the present invention can control the beam current value of the ion beam with which the irradiation object is to be irradiated to any desired value. The following describe a method for achieving that purpose.

The monitors 22 and 28 disposed along a beam orbit inside the irradiation nozzle 21 detect an ion beam that travels therethrough and output a detection signal to the irradiation controller 63. Based on the detection signal, the irradiation controller 63 calculates the beam current value of the ion beam and outputs the beam current value obtained through the calculation to the accelerator controller 62. The accelerator controller 62 compares a predetermined desired beam current value with the beam current value (the beam current value based on the detection signal from the monitors 22 and 28) received from the irradiation controller 63. When the beam current value based on the detection signal from the monitors 22 and 28 is smaller than the desired beam current value, the accelerator controller 62 controls the extraction radiofrequency power supply 8 to thereby increase radiofrequency intensity to be applied to the extraction radiofrequency electrode 7. When the beam current value based on the detection signal from the monitors 22 and 28 is greater than the desired beam current value, the accelerator controller 62 controls the extraction radiofrequency power supply 8 to thereby decrease the radiofrequency intensity to be applied to the extraction radiofrequency electrode 7. As such, the accelerator controller 62 controls the extraction radiofrequency power supply 8 to thereby adjust the radiofrequency intensity to be applied to the extraction radiofrequency electrode 7. This arrangement allows the beam current value of the ion beam extracted from the synchrotron 4 to be adjusted. By repeating this control, the extracted beam current value can be set to any desired value.

Figure 3:
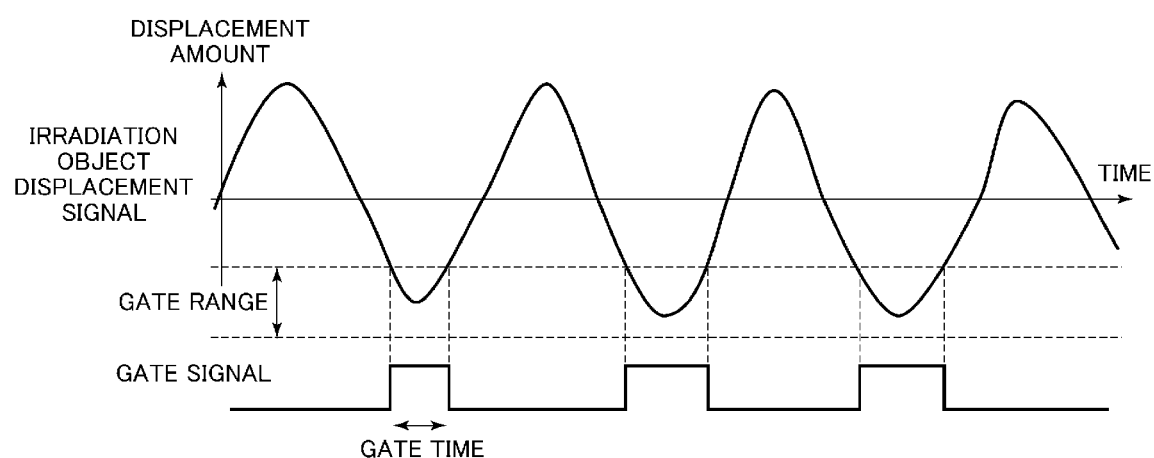
FIG. 3 is a diagram showing an example of generating a gate signal by an irradiation object monitoring system included in the charged particle irradiation system shown in FIG. 1.

The irradiation object monitoring unit 66 will be described with reference to FIG. 3. The irradiation object monitoring unit 66 is disposed in the irradiation room 17 and monitors the irradiation object 51. The irradiation object monitoring controller 65 is connected to the irradiation object monitoring unit 66 and thus controls the irradiation object monitoring unit 66. The irradiation object 51 makes a quasi-cyclical motion. The irradiation object monitoring unit 66 monitors the displacement of a surface of the irradiation object 51 by using a laser rangefinder and generates an irradiation object displacement signal like that shown in FIG. 3. The irradiation object monitoring unit 66 outputs a gate signal when an amplitude of the irradiation object displacement signal falls within a range (a gate range shown in FIG. 3) specified by the irradiation planning equipment 64. The gate range is specified by the irradiation planning equipment 64. In FIG. 3, a rising edge of the gate signal is a gate start signal and a falling edge of the gate signal is a gate end signal. The term "quasi-cyclical motion" is defined as an incomplete cyclical motion that is not completely reproducible, such as internal organs being displaced through breathing.

The preferred embodiment of the present invention described heretofore uses the laser rangefinder as the irradiation object monitoring unit 66. The irradiation object displacement signal may nonetheless be generated by using an X-ray image. Additionally, the irradiation object displacement signal may still be generated by measuring a displacement amount of the irradiation object by using infrared rays, measuring acceleration by using an acceleration sensor disposed on the surface of the irradiation object, or by measuring displacement inside the irradiation object by using ultrasonic waves. Alternatively, when the irradiation object is a patient, the irradiation object displacement signal may be generated by measuring a flow rate of air involved in breathing.

The dose distribution formed by the irradiation nozzle 21 according to the preferred embodiment of the present invention will be described with reference to FIGS. 4 through 10.

The dose distribution is realized by combining formation of the dose distribution in the lateral direction through beam scanning and formation of the dose distribution in the depth direction through energy change.

Figure 4:
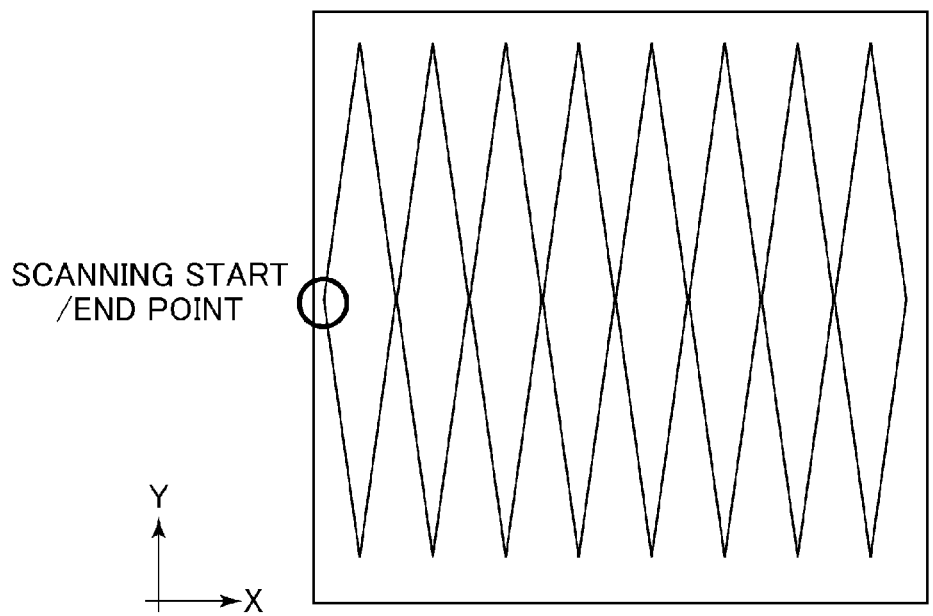
FIG. 4 is a diagram showing a typical path of an ion beam scanned by a scanning magnet included in the irradiation nozzle shown in FIG. 2.
Figure 5:
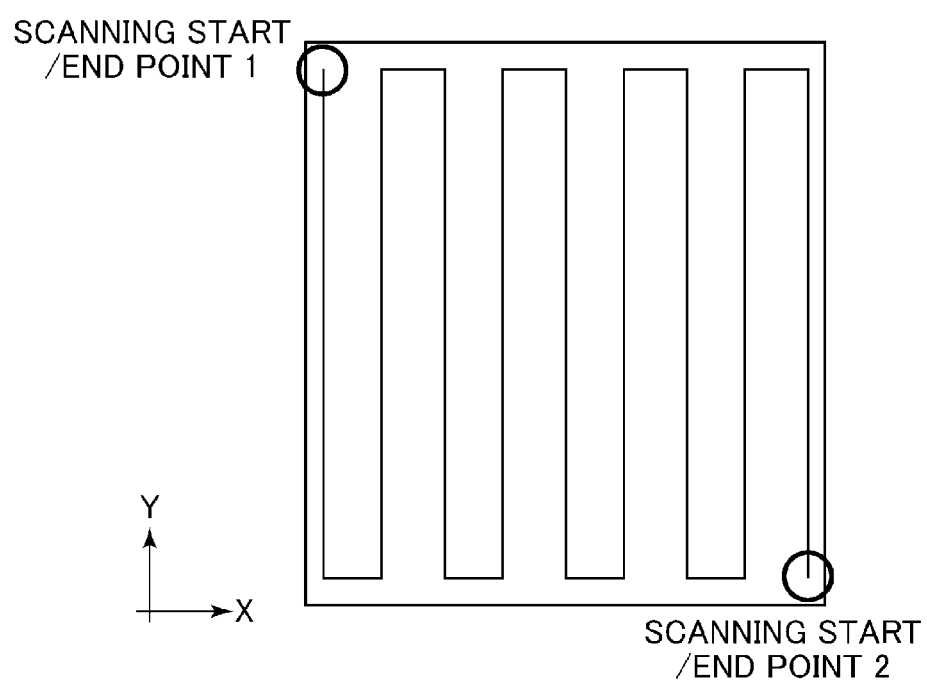
FIG. 5 is a diagram showing a typical path of the ion beam scanned by the scanning magnet included in the irradiation nozzle shown in FIG. 2.

A method of scanning the ion beam in the lateral direction by using the Y-axis scanning magnet 23 and the X-axis scanning magnet 24 in the irradiation nozzle 21 will be described first. FIGS. 4 and 5 are diagrams showing typical paths of the ion beam scanned by the scanning magnets. FIG. 4 shows a zigzag scanning path having a single point of a scanning start/end point. FIG. 5 shows a rectangular scanning path having two scanning start/end points. In the preferred embodiment of the present invention, a similar effect can be achieved regardless of whether the zigzag beam scanning (FIG. 4) or the rectangular beam scanning (FIG. 5) is performed. The irradiation nozzle 21 according to the preferred embodiment of the present invention uses the Y-axis scanning magnet 23 and the X-axis scanning magnet 24 to scan the ion beam whose diameter has been increased by the scatterer 25 along the path shown in FIG. 4 or 5 to thereby form the distribution in the lateral direction. The X-axis and the Y-axis extend perpendicularly to the beam axis, each indicating a direction orthogonal to each other.

Figure 6:
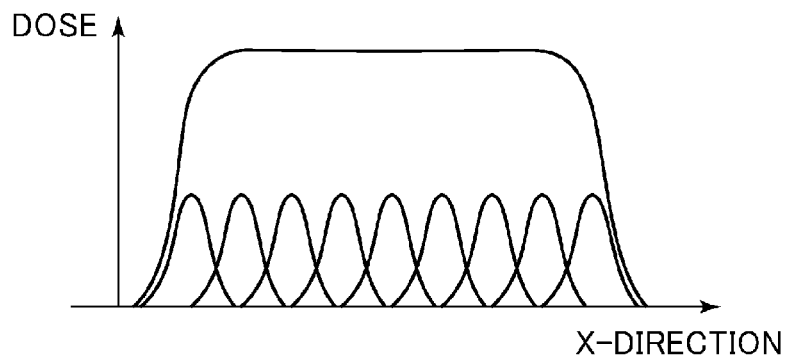
FIG. 6 is a graph showing a typical dose distribution in an X-axis direction according to the scanning path shown in FIG. 5.

FIG. 6 shows a dose distribution in the X-axis direction of FIG. 5. The dose distribution is uniform in the lateral direction as shown in FIG. 6. The irradiation method according to the preferred embodiment of the present invention forms an irradiation field by scanning the path shown in FIG. 4 or 5 a plurality of times by using a single energy. Scanning from one scanning start/end point to another shown in FIG. 4 or 5, specifically, a minimum unit of scanning for forming an irradiation field that is uniform in the lateral direction is called "one-plane irradiation (unit irradiation)". Repeating this one-plane irradiation is called "repainting irradiation".

The path shown in FIG. 4 is for scanning at a constant velocity at all times in each of the X-axis direction and the Y-axis direction, offering an advantage of easy control. The path shown in FIG. 5 permits the one-plane irradiation over a path shorter than that of FIG. 4. The preferred embodiment of the present invention requires scanning at a higher velocity on the Y-axis, so that the scanning magnet on an upstream of the beam is used to scan in the Y-direction.

Figure 7:
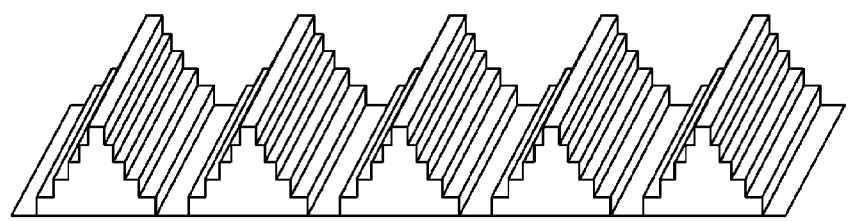
FIG. 7 is an illustration showing a general view of an energy filter included in the irradiation nozzle shown in FIG. 2.
Figure 8:
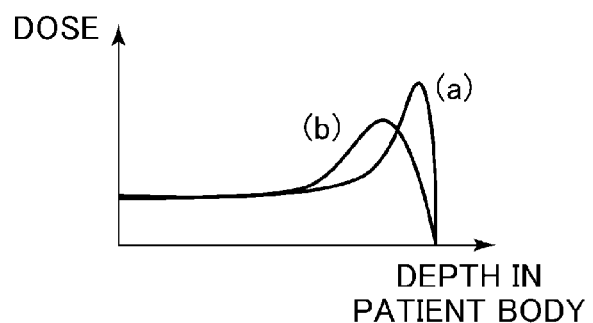
FIG. 8 is a graph showing a dose distribution in a depth direction obtained when the irradiation object shown in FIG. 2 is irradiated with an ion beam at one energy level using the irradiation nozzle shown in FIG. 2.
Figure 9:
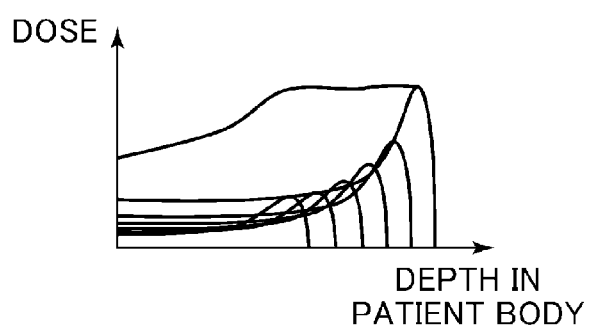
FIG. 9 is a graph showing a dose distribution in a depth direction obtained when an irradiation object is irradiated with an ion beam using an irradiation nozzle having no energy filter.
Figure 10:
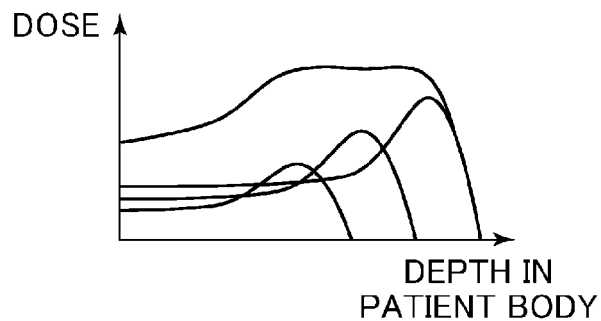
FIG. 10 is a graph showing a dose distribution in a depth direction obtained when an irradiation object is irradiated with an ion beam using an irradiation nozzle having an energy filter.

Irradiation of the ion beam in the beam traveling direction (the depth direction from the surface of the body) will next be described. In the depth direction, the energy filter 26 enlarges the bragg peak and the energy is changed to overlap the bragg peaks, thereby forming a uniform dose distribution. The dose distribution formed with a single energy is termed a layer. The energy filter 26 is wedge-shaped as shown in FIG. 7, having varying thicknesses according to the position in a direction perpendicular to the beam axis. The ion beam loses its energy that is variable according to the thickness of the energy filter 26. Reference numeral (a) in FIG. 8 shows the dose distribution in the depth direction when the energy filter 26 is not used and reference numeral (b) in FIG. 8 shows the dose distribution in the depth direction when the energy filter 26 is used. Because the energy filter 26 expands an energy distribution of the ion beam, a dose distribution with a milder bragg peak is formed. FIG. 9 is a graph showing a uniform dose distribution prepared by overlapping the energy distributions when the beams are extracted from the irradiation nozzle 21 having no energy filter 26 disposed therein ((a) of FIG. 8). FIG. 10 is a graph showing a uniform dose distribution prepared by overlapping the energy distributions when the beams are extracted from the irradiation nozzle 21 having the energy filter 26 disposed therein ((b) of FIG. 8). Whereas a bragg peak spacing in FIG. 9 is 5 mm or less, the bragg peak spacing in FIG.

10 is, for example, 1 cm or 2 cm, which is larger than in FIG. 9. In the embodiment, an irradiation target is divided into a plurality of layers in the depth direction (travelling direction of the ion beam in the patient's body), ion beam energy is changed according to depth (respective layers), and then the whole part of the irradiation target having a depthwise thickness is irradiated with desired ion beams. In this case, since the ion beam having passed through the energy filter 26 provided in the irradiation nozzle 21 is irradiated, the thickness of each layer of the irradiation target can be made larger. This can decrease the number of layers of the irradiation target to be divided depthwise and a desired dose distribution can be formed for a short period of treatment time. Further, the irradiation target is irradiated with the ion beam having passed through the energy filter 26. Thus the shape of the bragg peak is mild and the change in dose per unit length in the depth direction is small, so that dose uniformity is less sensitive to displacement or deformation of the irradiation object in the depth direction. Therefore dose uniformity is improved over the whole irradiation target area.

Factors contributing to the uniform dose distribution not obtainable when an irradiation target moving quasi-cyclically is irradiated through scanning irradiation will be described.

A method called gate irradiation has been used when a moving irradiation object 51 is to be irradiated. This method monitors displacement of the irradiation object 51 as the irradiation object 51 is displaced quasi-cyclically and performs irradiation only when the displacement falls within a predetermined phase (gate). The position of the irradiation object 51 at which the irradiation object 51 is irradiated with the ion beam through this method is limited, which ensures higher positioning accuracy in irradiation as compared with a method not using gate irradiation. Even with the gate irradiation, however, it is difficult to determine the position of the irradiation object 51 with an accuracy of a few mm or less, because part of the cyclical displacement of the irradiation object 51 is indeterminable. The displacement of a few mm is involved in the change in dose distribution.

Figure 11A:
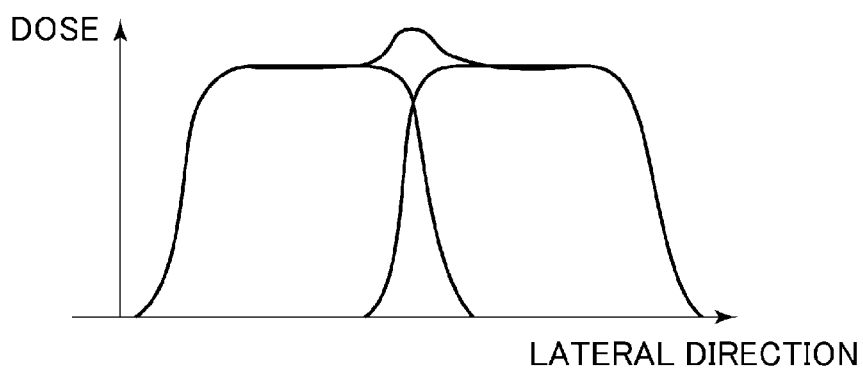
FIGS. 11A and 11B are graphs showing cases in which a uniform dose distribution in a lateral direction is not obtained, FIG. 11A showing a case in which a high dose region occurs and FIG. 11B showing a case in which a low dose region occurs.
Figure 11B:
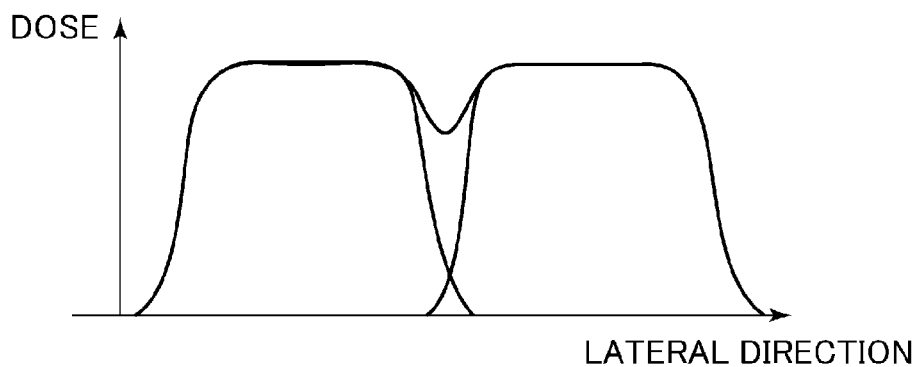

Uniformity in the direction perpendicular to the beam traveling direction, or in the lateral direction, will be described. Suppose that a gate is terminated and irradiation is interrupted in the middle of irradiation through ion beam scanning. If irradiation is resumed at the same time that the next gate is started, the position of the irradiation object 51 is likely to be deviated from where the irradiation object 51 was at the time when the irradiation was interrupted. If the irradiation positions overlap, therefore, a high dose region occurs as shown in FIG. 11A. If the irradiation position is deviated, on the other hand, a low dose region occurs as shown in FIG. 11B.

Figure 12:
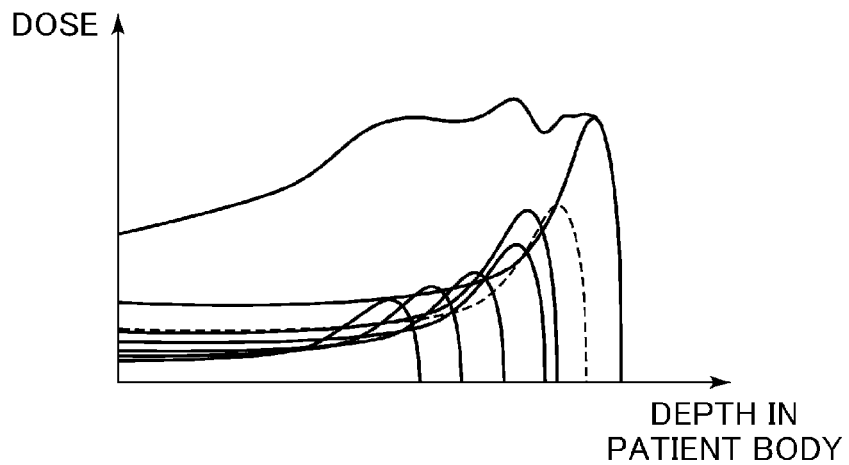
FIG. 12 is a graph showing a case in which a uniform dose distribution in a depth direction is not obtained.

Uniformity in the direction extending in parallel with the beam traveling direction, or in the depth direction (the depth direction from the surface of the body), will be described. An ion beam irradiation with a predetermined energy forms a dose distribution having a bragg peak. When the irradiation with that particular energy is completed, the synchrotron 4 accelerates the ion beam to the next energy and resumes irradiation; however, during the period of time in which energies of the ion beam are changed, the irradiation object is displaced, resulting in the distance in the depth direction between different bragg peaks being changed. FIG. 12 shows a dose distribution when the bragg peak indicated by the dotted line is shifted to a shallow side. If the bragg peak is shifted as in this case, a high dose region and a low dose region may also occur in the depth direction.

Because of the factors described above, the dose distribution may change and a uniform dose distribution may not be obtainable. The charged particle irradiation system (irradiation method) according to the preferred embodiment of the present invention can form a dose distribution that is uniform in the depth direction by forming a laterally uniform dose distribution, which is achieved by not interrupting one-plane irradiation in the middle of the irradiation, and by making the bragg peak mild using the energy filter 26 and decreasing fluctuations in the bragg peak position through repainting irradiation.

The irradiation planning equipment 64 has image data of the irradiation object 51 stored therein. The image data is previously imaged by an X-ray computed tomography (CT) system. Based on this image data, the irradiation planning equipment 64 displays the image of the irradiation object 51 including the irradiation target 52 on a display (not shown). An operator determines an irradiation dose required for the irradiation target 52, and an irradiation field shape of the irradiation target 52 based on this image data. The operator inputs the irradiation dose and the irradiation field shape from an input device (not shown). Receiving information on the irradiation dose and the irradiation field shape, the irradiation planning equipment 64 determines first parameters so as to form the irradiation dose and the irradiation field shape specified by the operator. The first parameters include an irradiation angle (angle of the rotating gantry), an ion beam energy, an amount of charge of the ion beam, an irradiation field size, a collimator shape, and a bolus shape, all of which is stored in a storage device. In the irradiation method according to the preferred embodiment of the present invention, the irradiation target 52 is irradiated with the ion beam by being divided into a plurality of layers $L_i$ (i=1, 2, . . . N) in the depth direction. The irradiation planning equipment 64 obtains a specific energy of the ion beam suitable for irradiation according to the depth of each layer. Because the irradiation is performed using a plurality of energies, the irradiation planning equipment 64 specifies all of the energies used for irradiation according to the depth of the irradiation target 52 in the irradiation object 51. To ensure that the irradiation target 52 is irradiated with a required dose, the amount of charge of the ion beam is determined for each energy. The irradiation planning equipment 64 stores information on the ion beam energies and the amount of charge in each energy determined, in the storage device.

The operator also specifies the number of repainting irradiations for each energy by using the input device. The information on the number of repainting irradiations inputted is transmitted to the irradiation planning equipment 64 and stored in the storage device. The number of repainting irradiations, as the term used here, represents the number of times the irradiation (repainting) is performed for a given layer in the irradiation target 52, with the ion beam scanning from the scanning start point to the scanning end point defined as one unit.

The irradiation object monitoring unit 66 (the laser rangefinder according to the preferred embodiment of the present invention) measures the displacement of the body surface of the irradiation object 51 lying on the couch 41 and generates an irradiation object displacement signal that serves as position information of the irradiation object 51. The irradiation object displacement signal is transmitted to the irradiation planning equipment 64 via the irradiation object monitoring controller 65. The irradiation planning equipment 64 displays the irradiation object displacement signal as shown in FIG. 3 on the display. The operator determines, based on the irradiation object displacement signal displayed on the display, the range of amplitude of the irradiation object displacement signal, or the gate range in which the irradiation object monitoring unit 66 outputs a gate signal, and specifies the gate range from the input device. The gate range specified by the operator is transmitted to the irradiation object monitoring controller 65. In addition, the irradiation planning equipment 64 obtains an average value of the irradiation object displacement signal based on the irradiation object displacement signal received. Then, based on the average value of the irradiation object displacement signal obtained and the gate range specified by way of the input device, the irradiation planning equipment 64 finds an average value of a gate time (an average gate time) during which the irradiation object displacement signal falls within the gate range. The average gate time obtained, together with other parameters required for irradiation, is transmitted to the central control unit 61 and stored in a storage device. According to the preferred embodiment of the present invention, the irradiation object monitoring unit 66 disposed in the irradiation room 17 is used to acquire the irradiation object displacement signal in advance; however, another irradiation object monitoring system disposed outside the irradiation room may be used to acquire the irradiation object displacement signal.

The beam current value is another piece of information required for irradiation, in addition to the parameters prepared by the irradiation planning equipment 64. Steps followed by the central control unit 61 to calculate the beam current value will be described below with reference to FIG. 13. The central control unit 61 receives in advance second parameters required for calculating the beam current value from the irradiation planning equipment 64. The second parameters are information including the ion beam energy, the amount of charge of the ion beam, the irradiation field size, the average gate time, the number of repainting irradiations, and the like. The central control unit 61 stores these second parameters in the storage device.

The central control unit 61 determines the beam current value for each energy in descending order of intensity of the energies, i.e. from high to low energy, of all the ion beams with which the irradiation object 51 is irradiated. Specifically, the central control unit 61 finds the beam current value for each layer of the plurality of layers $L_i$ (i=1, 2, ... N) into which the irradiation target 52 is divided in the beam traveling direction, in ascending order of depth starting with the layer at the position deepest from the body surface (a deepest layer $L_1$). A technique to find the beam current value at each layer will be described below with reference to a flowchart shown in FIG. 13.

Figure 13:
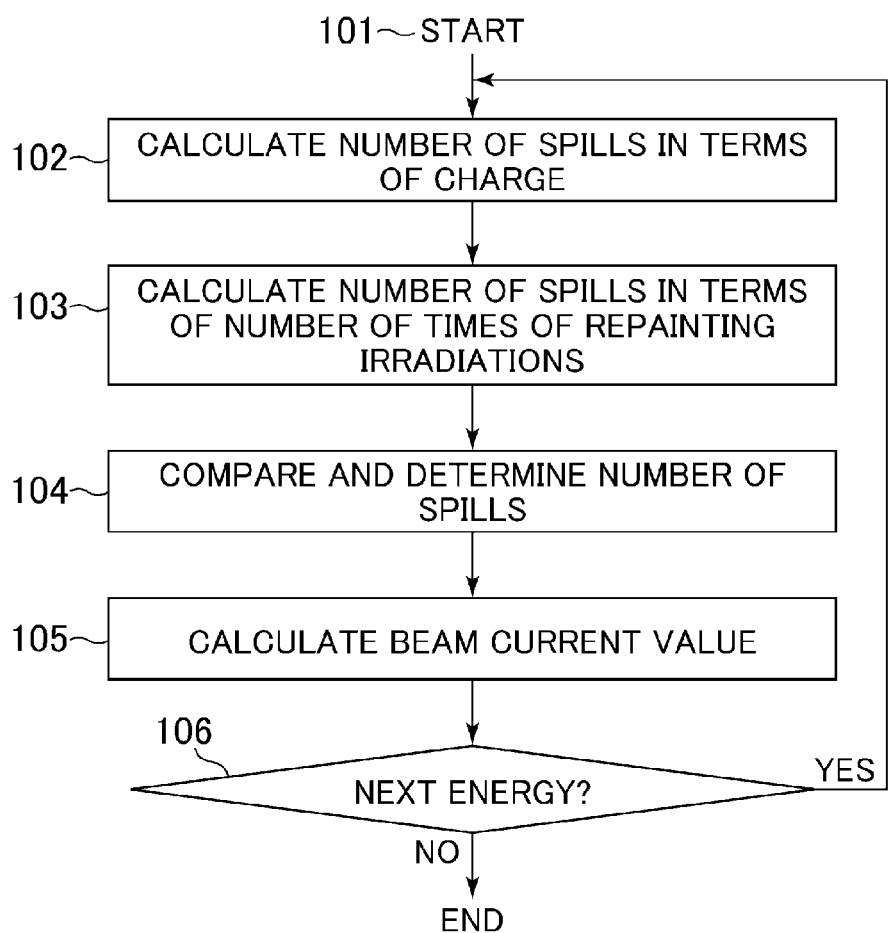
FIG. 13 is a flowchart showing steps followed by a central control unit shown in FIG. 1 to calculate an extraction beam current value of the ion beam.

The technique starts with step 101 of FIG. 13. Then, in step 102, the central control unit 61 finds the number of spills in terms of the amount of charge of the ion beam. Specifically, the central control unit 61 first reads information on the amount of charge of the ion beam to be extracted from the synchrotron 4 in a single cycle (one spill) (a first amount of charge) and the amount of charge required for irradiating a layer $L_i$ of the irradiation target 52 (a second amount of charge) stored previously in the storage device. The central control unit 61 divides the second amount of charge by the first amount of charge and sets a value obtained by rounding up to the nearest whole number as the number of spills in terms of the amount of charge of the ion beam. For example, assume that the amount of charge of the ion beam to be extracted from the synchrotron 4 per one spill (one operating cycle) is 10 [nC] and the amount of charge of the ion beam required for the layer $L_i$ of the irradiation target 52 is 35 [nC]. In such cases, divide the second amount of charge of 35 [nC] by the first amount of charge of 10 [nC] to obtain 3.5; then round up 3.5 to the nearest whole number to arrive at 4. The value of 4 is the number of spills in terms of the amount of charge of the ion beam. Specifically, the required number of spills is 4 when irradiating the layer $L_i$ with the ion beam.

Then in step 103, the central control unit 61 finds the number of spills in terms of the number of repainting irradiations. Specifically, the central control unit 61 first reads information on the average gate time and one-plane irradiation time from the storage device. Note here that the information on the average gate time is included in the second parameters and previously stored in the storage device. The one-plane irradiation time represents irradiation time required for irradiating any given layer $L_i$ of the irradiation target 52 (time required for one-plane irradiation). The one-plane irradiation time varies according to the scanning speed of the ion beam which the Y-axis scanning magnet 23 and the X-axis scanning magnet 24 scan and the size of the irradiation field. Based on the scanning speed of the ion beam and the size of the irradiation field of the irradiation target 52, the central control unit 61 finds the one-plane irradiation time for each layer and stores in advance the one-plane irradiation time in the storage device. The central control unit 61 divides the average gate time read in step 103 by the one-plane irradiation time and rounds up what is obtained from the division process to the nearest whole number to arrive at the number of repainting irradiations (a first number of repainting irradiations) per spill. The first number of repainting irradiations obtained through the foregoing calculation indicates the number of repainting irradiations to be performed relative to the layer $L_i$ of the irradiation target 52 during one operation cycle of the synchrotron 4. The central control unit 61 then reads from the storage device information on the number of repainting irradiations required for the layer $L_i$ of the irradiation target 52 (a second number of repainting irradiations). The second number of repainting irradiations is a value received from the irradiation planning equipment 64. This value represents the number of repainting irradiations (determined to be necessary for forming a uniform dose distribution) specified by the operator and stored in advance in the storage device. The central control unit 61 divides the required number of repainting irradiations (the second number of repainting irradiations) by the number of repainting irradiations per spill to arrive at a quotient. The central control unit 61 determines the quotient to be the number of spills in terms of the number of repainting irradiations. Assume, for example, that the average gate time based on a signal indicative of displacement of the irradiation object (patient) is 0.5 [seconds] and the one-plane irradiation time relative to the layer $L_i$ is 0.1 [seconds]. In such a case, the central control unit 61 determines the number of repainting irradiations (the first number of repainting irradiations) to be performed per spill to be five. If the number of repainting irradiations required for the layer $L_i$ is 50, then the central control unit 61 divides the second number of repainting irradiations that is 50 by the first number of repainting irradiations that is 5 to arrive at a quotient of 10 and determines the value of 10 to be the number of spills in terms of the number of repainting irradiations.

In step 104, the central control unit 61 compares the number of spills obtained in step 102 with the number of spills obtained in step 103 and determines whichever is greater to be the number of spills required for irradiation. For example, if, as described earlier, the number of spills in terms of the amount of charge of the ion beam obtained in step 102 is 4 and the number of spills in terms of the number of repainting irradiations obtained in step 103 is 10, then the central control unit 61 determines the number of spills required for irradiation to be 10.

In step 105, the central control unit 61 finds the beam current value and the maximum number of repainting irradiations per spill. Specifically, the central control unit 61 finds a product of the number of spills required for irradiation obtained in step 104, the number of repainting irradiations per spill obtained in step 103, and the one-plane irradiation time and determines the obtained product to be time (extraction time) during which the ion beam is to be extracted to the layer $L_i$. Then, the central control unit 61 determines the number of charge required per spill for the layer $L_i$ to be a value obtained by dividing the total amount of charge (second amount of charge) required to irradiate the layer $L_i$ by the number of spills required for irradiation obtained in step 104. The central control unit 61 divides the number of charge required per spill by the extraction time and determines the quotient obtained through the foregoing calculations to be the beam current value. Similarly, the central control unit 61 determines the number of repainting irradiations per spill obtained in step 103 to be the maximum number of repainting irradiations per spill. The central control unit 61 stores the beam current value and the maximum number of repainting irradiations per spill obtained in step 105 in the storage device. By setting the maximum number of repainting irradiations per spill as in the preferred embodiment of the present invention, preventing a occurrence of a situation in which a required beam current cannot be obtained for short of charge during irradiation is possible.

When the central control unit 61 allows the storage device to store a beam current value and the maximum number of repainting irradiations for a layer $L_i$, in step 106, the central control unit 61 determines whether a layer $L_{i+1}$ associated with the subsequent energy is present or not. If the central control unit 61 determines that the subsequent energy is present, then the central control unit 61 returns to step 102 and executes steps 102 through 105 to obtain a beam current value and the maximum number of repainting irradiations for the layer $L_{i+1}$. The foregoing calculations are performed for each of all energies (for all layers $L_i$ (i =1, 2, . . . N). In step 106, If the central control unit 61 determines that a layer associated with the subsequent energy is not present, then the central control unit 61 terminates calculation for the beam current value and the maximum number of repainting irradiations.

Through the foregoing calculations, there may be a layer for which no repainting irradiation is performed. For a shallow layer with a small amount of irradiation and a short average gate time, the number of repainting irradiations may be one as a result of the above-mentioned calculations.

If it is found in step 106 that there are other energies left, the central control unit 61 returns to step 102 and repeats the calculations. If the number of spills calculated in step 103 is adopted in step 104, because of an allowance for the charge, an even greater value may be set for the maximum number of repainting irradiations per spill.

In the embodiment, the beam current value is calculated for respective energies (respective layers $L_i$) as described above. This allows the number of repainting irradiations specified by the irradiation planning equipment 64 to be met, and the ion beam irradiation at the maximum beam current in which the amount of charge of the ion beam to be extracted is taken into consideration. The ion beam irradiation at the maximum beam current shortens the irradiation time and, accordingly, time to restrain the irradiation object, so that the irradiation object can be relieved of some burden. Further, treatment time it takes per patient is reduced and a number of patients can be treated, which leads to improvement in throughput of the patient.

After having calculated the beam current value, the central control unit 61 transmits necessary information to the accelerator controller 62 and the irradiation controller 63. The central control unit 61 transmits the energy and beam current values of the ion beam to the accelerator controller 62 and the amount of charge and energy of the ion beam and the size of the irradiation field to the irradiation controller 63. The irradiation controller 63 calculates position, width, amount of charge, and the beam current value of the ion beam based on data acquired from the monitors 22 and 28 of the irradiation nozzle 21 and transmits an extraction start signal, an extraction stop signal, and the beam current value to the accelerator controller 62. In addition, the irradiation controller 63 controls an energization current by controlling an energization power source (not shown) that energizes the Y-axis scanning magnet 23 and the X-axis scanning magnet 24, thereby changing the position which the ion beam reaches in the lateral direction. The irradiation controller 63 also receives the gate signals from the irradiation object monitoring unit 66. The start of the gate is the gate start signal, while the end of the gate is the gate end signal.

Through the foregoing processes, all parameters necessary for irradiation are determined by the irradiation planning equipment 64 and the central control unit 61 and set in the accelerator controller 62 and the irradiation controller 63. Irradiation is then ready as soon as a couch 1 on which the irradiation object 51 are placed is located in place.

Steps for the ion beam irradiation will be described with reference to FIG. 14. When all preparations for irradiation are made, the operator presses an irradiation start button on the central control unit 61 to thereby start a series of irradiations in step 111. The central control unit 61 first transmits an acceleration signal to the accelerator controller 62 and the irradiation start signal to the irradiation controller 63. The accelerator controller 62 performs the following control to accelerate the ion beam to the energy used for irradiation. The ion beam injected from the ion source into the linear accelerator is pre-accelerated and then injected into the synchrotron 4. The ion beam injected in the synchrotron 4 travels around the orbit in the synchrotron 4 and is accelerated by the acceleration unit 6 to the energy specified by the irradiation planning equipment 64. On completing the acceleration of the ion beam, the accelerator controller 62 transmits an extraction start signal to the irradiation controller 63. When receiving the irradiation start signal from the central control unit 61, the irradiation controller 63 controls the scanning magnets 23 and 24 to the scanning start point such that the ion beam is scanned. When the gate start signal is received in step 112 after the extraction start signal has been received, the one-plane irradiation is performed in step 113. Specifically, the irradiation controller 63 transmits an extraction permission signal to the accelerator controller 62 and beam scanning is started. On receipt of the extraction permission signal from the irradiation controller 63, the accelerator controller 62 uses the radiofrequency acceleration unit 5 to apply radiofrequency to the accelerated ion beam. The ion beam is extracted by the extraction deflector 11. During extraction of the beam, the irradiation controller 63 continues transmitting a beam current value calculated from a dose monitor signal to the accelerator controller 62. The accelerator controller 62 controls the radiofrequency acceleration unit 5 by referring to the beam current value received from the irradiation controller 63 to thereby make the ion beam be extracted at the beam current value specified by the central control unit 61. Checks are made for steps from 114 to 116 for each one-plane irradiation and, if all are answered in the negative, the operation returns to step 113 and the next one-plane irradiation is performed continuously. Step 114 is to check that the number of repainting irradiations by the energy being used for irradiation reaches the number specified by the irradiation planning equipment 64. Step 115 is to check that the number of repainting irradiations during a single cycle reaches the maximum number of repainting irradiations per spill. Step 116 is to check that the gate end signal is received during one-plane irradiation. When step 115 or 116 is answered in the affirmative, the synchrotron 4 decelerates and accelerates the ion beam to store charge anew and the operation proceeds to step 112 and irradiation is resumed with the next gate start signal. When step 114 is answered in the affirmative, it is determined whether the next energy is available or not in step 117. When it is determined that the next energy is available, the operation returns to step 112 and irradiation is started with the next energy. When it is determined that there is no more energy, the irradiation sequence is completed.

Figure 14:
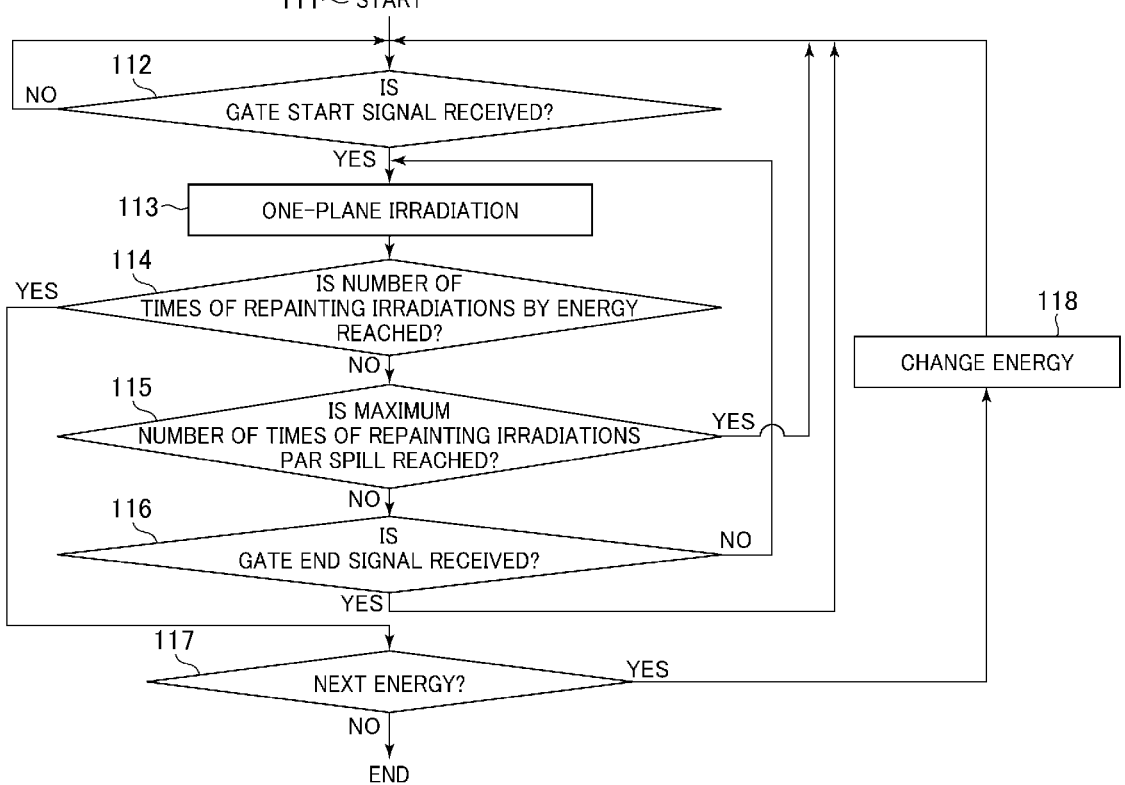
FIG. 14 is a flowchart showing irradiation steps.
Figure 15:
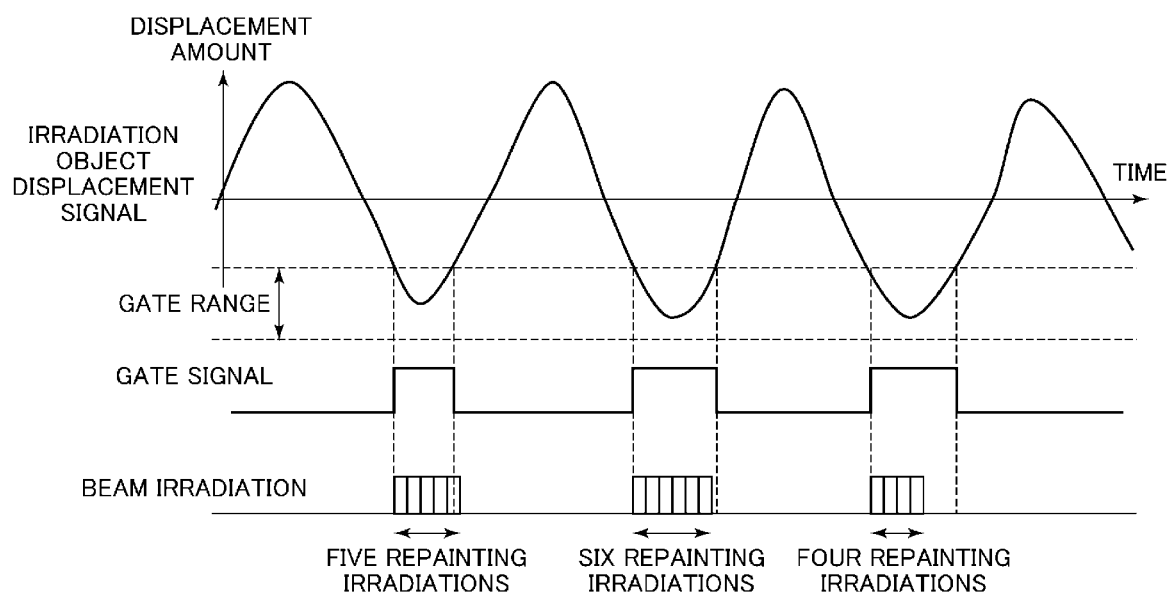
FIG. 15 is a diagram showing typical timing of ion beam irradiation.

FIG. 15 is a diagram showing typical timing for irradiation performed according to the flowchart shown in FIG. 14. The irradiation object displacement signal and the gate signal are the same as those in FIG. 3. FIG. 15 shows irradiation with a single energy, with the maximum number of repainting irradiations per spill being six and the number of repainting irradiations per energy being 15. One rectangle on a beam irradiation axis denotes one-plane irradiation. In the first spill, one-plane irradiation is started with the gate start. Because the gate ends during the fifth one-plane irradiation, irradiation by the first spill is completed upon completion of the fifth one-plane irradiation. The gate does not end upon completion of the sixth repainting irradiation for the second spill; however, because the maximum number of repainting irradiations per spill is six, the second spill ends at the sixth repainting irradiation. For the third spill, the number of repainting irradiations per energy of 15 is reached by the four repainting irradiations. Irradiation by the third spill is therefore terminated by the four repainting irradiations.

Advantages of the irradiation method according to the preferred embodiment of the present invention will be described below.

To form a laterally uniform dose distribution, the lateral one-plane irradiation time is shortened and irradiation is continued until the one-plane irradiation is completed even after the gate ends. This process eliminates a situation in which the dose distribution is changed by a joint between dose distributions in the lateral direction. The irradiation after the gate ends cancels an effect from limiting the irradiation position by the gate irradiation; however, shortening the one-plane irradiation time shortens the irradiation time after the gate ends, which achieves the effect of the gate irradiation. In addition, setting a small gate range allows the effect of gate irradiation to be achieved even when the irradiation is performed after the gate ends.

To form a dose distribution that is uniform in the depth direction, the energy filter 26 is used to perform repainting irradiation. Performing the repainting irradiation results in the bragg peak formed with one energy being an overlap of the bragg peaks formed through one-plane irradiation. Performing the repainting irradiation more results in the position of overlapping bragg peaks being steady and the distance between different bragg peaks being made closer to a degree. In addition, widening the width of the bragg peak with the energy filter 26 allows the amount of change in dose per unit length in the depth direction to be made small. Specifically, the dose distribution has a mild gradient in the depth direction. The dose distribution having a mild gradient exhibits a small change in dose relative to the displacement of the bragg peak position in the depth direction, so that a uniform dose distribution can be formed.

The preferred embodiment of the present invention uses the scatterer 25 to perform continuous scanning. Use of the scatterer 25 shortens the scanning path, resulting in a shorter one-plane irradiation time. The shorter one-plane irradiation time shortens the irradiation time after the gate ends. Furthermore, the shorter one-plane irradiation time helps make the displacement of the irradiation object small within the one-plane irradiation time, so that effect on uniformity can be minimized. Additionally, the use of the scatterer 25 helps make small the change in dose per unit distance in the lateral direction, so that a uniform distribution can be more easily obtained even if the irradiation object is displaced or the position of the ion beam fluctuates. Further, the shorter one-plane irradiation time helps increase the number of repainting irradiations possible during a predetermined period of time.

The preferred embodiment of the present invention uses the energy filter 26. The energy filter 26 makes the bragg peak mild. This allows a dose distribution less sensitive to displacement in the depth direction to be formed and decreases the number of energies required for forming the dose distribution. The decreased number of energies elongates the irradiation time using a single energy. The longer irradiation time increases the number of repainting irradiations.

A solution according to the method of the preferred embodiment of the present invention to the problem associated with the method disclosed in JP-2008-154627-A will be described. The method according to the preferred embodiment of the present invention achieves uniformity by considerably increasing the number of repainting irradiations. A uniform irradiation field can therefore be formed within a short period of time even if the displacement waveform of the irradiation object is not stable, which is the problem associated with the method disclosed in JP-2008-154627-A.

According to the irradiation method of the preferred embodiment of the present invention, the dose uniformity is achieved by increasing the number of repainting irradiations. Irradiation is therefore continued even when the displacement waveform of the irradiation object is not stable, as long as the displacement falls within the gate range. Consequently, there is no likelihood that the irradiation time will be long. Further, the irradiation is performed with the beam current value that is determined in consideration of the amount of charge of the ion beam to be extracted per cycle. The irradiation method is therefore applicable to a case in which the amount of charge of the ion beam to be extracted per cycle is limited.

According to the present embodiment, the central control unit determines a beam current value for each energy (respective layer) in consideration of the amount of charge of the ion beam to be extracted per spill for the synchrotron and determines the maximum number of repainting irradiations per spill. Therefore, irradiation of the ion beam is not interrupted in the middle of the one-plane irradiation for respective layers. It is, therefore, possible to prevent a reduction in uniformity in dose distribution that would otherwise occur due to interruption of ion beam irradiation.

The preferred embodiment of the present invention has been described for an arrangement including the synchrotron used for the ion beam generator. A cyclotron or other accelerator may still be used. If the limit imposed on the amount of charge to be used within one cycle of, for example, the cyclotron is negligible, a uniform irradiation field can be formed within a short period of time by performing irradiation according to the method of the preferred embodiment of the present invention with the maximum number of repainting irradiations per spill set to be infinity.

Figure 16:
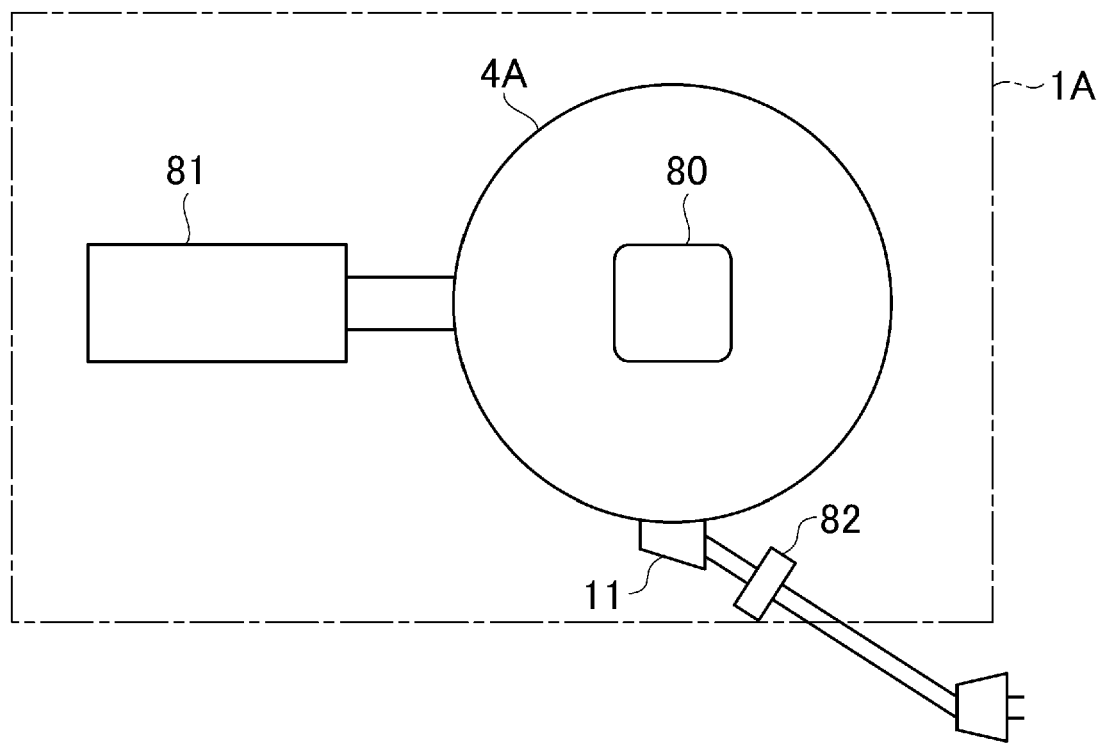
FIG. 16 is a diagram showing an arrangement of an ion beam generator included in the charged particle irradiation system which is another embodiment of the present invention.

A charged particle irradiation system using a cyclotron has another configuration. Specifically, in the system, the ion beam generator 1 of the charged particle irradiation system implemented in the first embodiment is replaced with the ion beam generator 1A shown in FIG. 16. The ion beam generator 1A includes an ion source 80, a cyclotron 4A, a beam acceleration system 81, and an energy absorber 82. The ion beam generated by the ion source 80 is accelerated by the cyclotron 4A to a predetermined energy and the energy of the ion beam is adjusted by the energy absorber 82. The ion beam is then transported by a beam transport line 2 to an irradiation nozzle 21. At this time, the beam current can be adjusted to any desired value by changing the output of the ion source 80.

According to the preferred embodiment of the present invention, the energy of the ion beam extracted from the ion beam generator is varied to change the energy of the ion beam reaching the irradiation object. The energy of the ion beam reaching the irradiation object may be changed by disposing the energy absorber in the irradiation nozzle or in the beam transport line.

In the preferred embodiment of the present invention, the central control unit 61 calculates the beam current value. The irradiation planning equipment 64 may, instead, be employed to calculate the beam current value by storing information that is previously stored in the central control unit 61 also in the irradiation planning equipment 64.

The foregoing descriptions of the preferred embodiment of the present invention assume that the beam current value remains constant within a single cycle and the dose of the layer irradiated with a single energy is constant in the lateral direction. The invention may still be applicable to a case in which a dose distribution is not constant. To form a non-constant dose distribution, a method is available to change the beam current value for each irradiation position or to change the scanning path and scanning speed.

In addition, the irradiation field may be formed without using any collimator or bolus by performing irradiation without using the scatterer 25. This method, however, requires that the number of repainting irradiations be increased in order to achieve uniformity and involves a longer irradiation time as compared with the arrangement using the scatterer 25.

What is claimed is:

1. A charged particle irradiation system, comprising:
    an ion beam generator in which a target beam current value is set and from which an ion beam is extracted with the target beam current value;
    an irradiation nozzle for irradiating an irradiation object with the ion beam, the irradiation nozzle including:
        a scanning magnet for scanning an ion beam passing therethrough; and
        an energy filter for increasing a width in a depth direction of a bragg peak formed by the ion beam; and
    an irradiation object monitoring unit for measuring a position of the irradiation object and outputting signals that vary with time according to displacement of the irradiation object;
    wherein the charged particle irradiation system determines extraction timing of the ion beam based on the signal outputted from the irradiation object monitoring unit and sequentially changes energies of the ion beam and performing a repainting irradiation with at least one of the energies.

2. The charged particle irradiation system according to claim 1, wherein:
    the irradiation object monitoring unit outputs a gate signal when the irradiation object falls within a specified range; and
    the extraction timing of the ion beam starts upon a start of the gate signal outputted from the irradiation object monitoring unit and ends with completion of a unit irradiation after the gate signal ends.

3. The charged particle irradiation system according to claim 1, wherein:
    the ion beam generator includes a synchrotron that accelerates the ion beam; and
    the synchrotron extracts the ion beam therefrom with the target beam current value determined based on an amount of charge required for irradiating with each of the energies, the number of times of repainting irradiations specified for each of the energies, an average value of a gate time during which the gate signal outputted from the irradiation object monitoring unit falls within a predetermined range, an amount of charge of the ion beam to be extracted per one operating cycle of the synchrotron, and a one-plane irradiation time.

4. The charged particle irradiation system according to claim 3, wherein:
    the synchrotron extracts the ion beam therefrom for each of the energies based on the target beam current value determined by the irradiation planning equipment.

5. The charged particle irradiation system according to claim 1, wherein:
    the ion beam generator includes a cyclotron that accelerates the ion beam; and
    the cyclotron extracts the ion beam therefrom with the target beam current value determined based on an amount of charge required for irradiating with each of the energies, the number of times of repainting irradiations specified for each of the energies, an average value of a gate time during which the gate signal outputted from the irradiation object monitoring unit falls within a predetermined range, and a one-plane irradiation time.

6. The charged particle irradiation system according to claim 1, wherein:
    the irradiation nozzle includes a scatterer adapted such that the ion beam passing therethrough is increased in diameter.

7. The charged particle irradiation system according to claim 1, wherein:
    the scanning magnet includes a first scanning magnet disposed upstream relative to a traveling direction of the ion beam and a second scanning magnet disposed downstream of the first scanning magnet; and
    the first scanning magnet changes a scanning position on the irradiation object in a shorter time than the second scanning magnet.

8. The charged particle irradiation system according to claim 1, wherein:
    the repainting irradiation is performed more than the specified number of times of repainting irradiations for each of the energies of the ion beam.

9. The charged particle irradiation system according to claim 1, wherein:
    the scanning magnet does not stop scanning during beam extraction.

10. The charged particle irradiation system according to claim 1, wherein:
    the ion beam generator extracts the ion beam therefrom for each of the energies based on the target beam current value determined by irradiation planning equipment.

* * * * *